(12) United States Patent
Pathak et al.

(10) Patent No.: US 10,692,011 B2
(45) Date of Patent: Jun. 23, 2020

(54) ADAPTIVE MODEL-BASED SYSTEM TO AUTOMATICALLY QUANTIFY FALL RISK

(71) Applicant: Verily Life Sciences LLC, Mountain View, CA (US)

(72) Inventors: Anupam Pathak, Los Altos Hills, CA (US); Ali Shoeb, Mill Valley, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 516 days.

(21) Appl. No.: 15/003,633

(22) Filed: Jan. 21, 2016

(65) Prior Publication Data

US 2017/0213145 A1    Jul. 27, 2017

(51) Int. Cl.
| | | |
|---|---|---|
| G06N 20/00 | (2019.01) | |
| G06N 7/00 | (2006.01) | |
| G06N 5/04 | (2006.01) | |
| G16H 50/30 | (2018.01) | |

(52) U.S. Cl.
CPC ............... *G06N 20/00* (2019.01); *G06N 5/04* (2013.01); *G06N 7/005* (2013.01); *G16H 50/30* (2018.01)

(58) Field of Classification Search
CPC ...................................................... G16H 50/30
See application file for complete search history.

(56) References Cited

U.S. PATENT DOCUMENTS

| | | | |
|---|---|---|---|
| 7,558,622 B2 | 7/2009 | Tran | |
| 9,107,586 B2 | 8/2015 | Tran | |
| 2005/0182305 A1* | 8/2005 | Hendrich | A61B 5/00 600/300 |
| 2006/0106743 A1* | 5/2006 | Horvitz | G08G 1/0104 706/21 |
| 2008/0009686 A1 | 1/2008 | Hendrich | |
| 2008/0186189 A1* | 8/2008 | Azzaro | A61B 5/1113 340/573.7 |
| 2011/0082672 A1 | 4/2011 | Hardigan | |
| 2011/0230791 A1 | 9/2011 | Ten Kate et al. | |
| 2012/0101411 A1 | 4/2012 | Hausdorff et al. | |

(Continued)

FOREIGN PATENT DOCUMENTS

EP    2329470 B1    4/2013

OTHER PUBLICATIONS

PCT/US2017/012576, International Search Report and Written Opinion of the International Searching Authority, dated Mar. 17, 2017, 15 pages.

(Continued)

*Primary Examiner* — Li B. Zhen
*Assistant Examiner* — Markus A. Vasquez
(74) *Attorney, Agent, or Firm* — Christensen O'Connor Johnson Kindness PLLC (57) ABSTRACT

A method predicts the fall risk of a user based on a machine learning model. The model is trained using data about the user, which may be from wearable sensors and depth sensors, manually input by the user, and received from other types of sources. Data about a population of users and data from structured tests completed by the user can also be used to train the model. The model uses features and motifs discovered based on the data that correlate to fall risk events to update fall risk scores and predictions. The user is provided a recommendation describing how the user can reduce a predicted fall risk for the user.

20 Claims, 8 Drawing Sheets

(56) References Cited

U.S. PATENT DOCUMENTS

| | | |
|---|---|---|
| 2013/0246088 A1 | 9/2013 | Huster et al. |
| 2014/0066816 A1 | 3/2014 | McNames et al. |
| 2014/0155705 A1 | 6/2014 | Papadopoulos et al. |
| 2014/0276130 A1* | 9/2014 | Mirelman ............ A61B 5/744 600/483 |
| 2014/0303508 A1 | 10/2014 | Plotnik-Peleg et al. |
| 2015/0272482 A1 | 10/2015 | Houmanfar et al. |
| 2017/0000387 A1* | 1/2017 | Forth ................ A61B 5/1117 |
| 2017/0039335 A1* | 2/2017 | Ismail ................ G16H 50/70 |
| 2017/0055917 A1* | 3/2017 | Stone ................ A61B 5/7275 |
| 2018/0357879 A1* | 12/2018 | Negre ............ A62B 35/0075 |

OTHER PUBLICATIONS

Qiu, H. et al., "Center-of-Pressure Based Postural Sway Measures: Reliability and Ability to Distinguish Between Age, Fear of Falling and Fall History", International Journal of Industrial Ergonomics (2015), http://dx.doi.org/10.1016/j.ergon.2015.02.004., May 1, 2015, pp. 37-44.

Provisional Application as filed for U.S. Appl. No. 61/970,482, filed Mar. 26, 2014, 14 pages.

* cited by examiner

ADAPTIVE MODEL-BASED SYSTEM TO AUTOMATICALLY QUANTIFY FALL RISK

FIELD OF ART

This disclosure relates generally to assessing the fall risk of patients and particularly to an adaptive system to automatically quantify fall risk.

BACKGROUND

Injuries caused by falling impact many people today, especially the elderly. The resulting hospitalizations are responsible for a significant resource cost to health care systems. Though there are factors tied to a greater risk of falls, these factors are not easily measured and assessed for each individual. Further, fall tracking is not commonplace, and most falls are self-reported by the patient to a physician, if reported at all. Individuals with neurological disorders such as Parkinson's disease and multiple sclerosis have a greater risk of falling because symptoms of these diseases have a toll on their central nervous systems and motor systems.

Existing systems can detect when an individual falls, and seek assistance for the individual. However, these systems are reactive measures, and a proactive solution currently does not exist. Further, existing systems do not generate recommendations regarding how an individual can reduce their risk of falling. Not only is it important to detect the fall, but also to monitor an individual's behavior on a regular basis to assess their fall risk over time and predict when they may be more vulnerable to falling. Since many elderly individuals live on their own, it is important for others (e.g., caretaker and family members) to have a way to remotely monitor the well-being of the individual and respond with appropriate help if the individual has fallen, which current systems do not provide.

SUMMARY

A system is provided to determine fall risk including an adaptive model for automatically predicting the fall risk of a user. The system trains a model using machine learning techniques and various features including, but not limited to, user inputs (e.g., age, vision, use of assistive devices in walking, etc.), sensor data (e.g., data collected from sensors associated with the user), external source data (e.g., population data about fall risk of a population of users), and in some cases structured user tests (e.g., tests performed by the user occasionally over time to assess sway radius and other conditions of the user on that day). Sensor data can be recorded from depth sensors, microphones, depth sensors, and a variety of wearable sensors on the user. The wearable sensors can be in the form of a wristband, wristwatch, pendant of a necklace, or belt clip. Data may be uploaded and synchronized to a cloud server where the fall risk model is updated. A notification or other feedback generated from the system can be sent to the user, the user's caregivers and other health care providers, the user's family and friends, and the like. The notification or feedback may include the user's fall risk as well as recommendations regarding how the user can reduce the risk of falling.

The figures depict various embodiments of the invention for purposes of illustration only. One skilled in the art will readily recognize from the following discussion that alternative embodiments of the structures and methods illustrated herein may be employed without departing from the principles of the invention described herein.

DETAILED DESCRIPTION

System Overview

Figure 1:
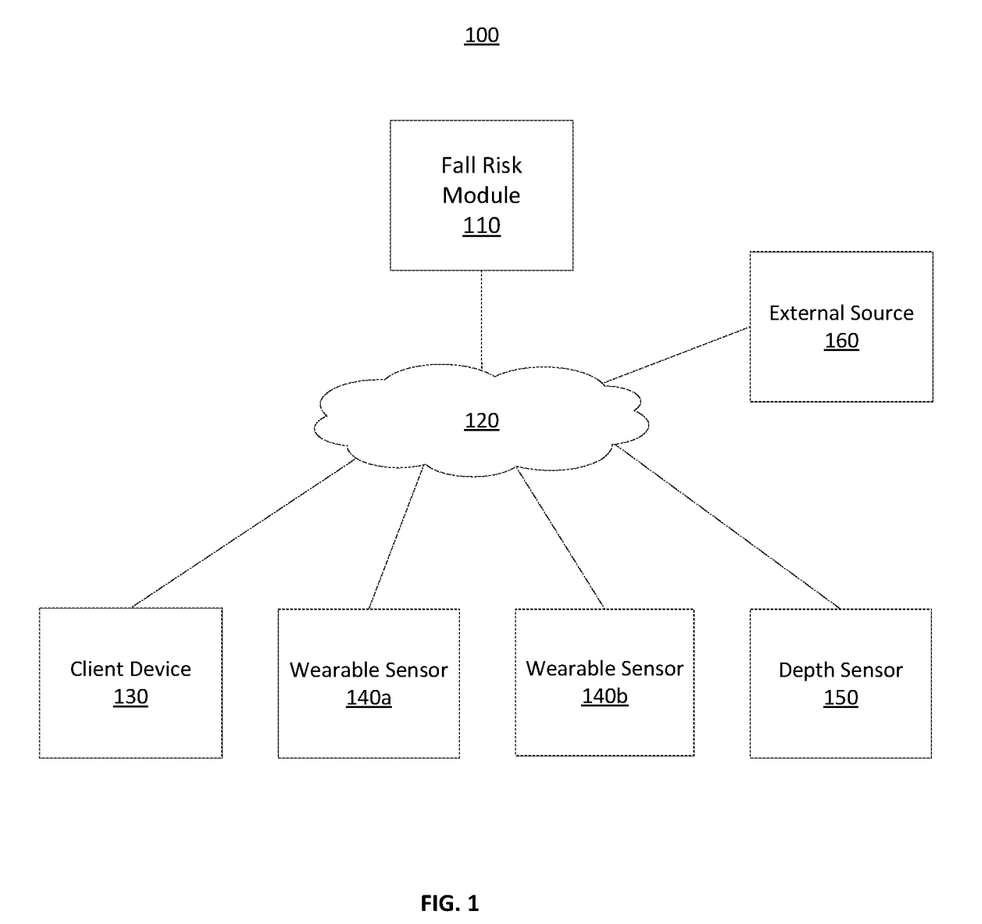
FIG. 1 is a block diagram of a computing environment of an adaptive system to automatically quantify fall risk, according to one embodiment.

FIG. 1 is a block diagram of a computing environment 100 of an adaptive system to automatically quantify fall risk according to one embodiment. The embodiment illustrated in FIG. 1 includes a fall risk module 110, a client device 130, wearable sensors 140 (e.g., 140a and 140b), a depth sensor 150, and an external source 160 connected to each other by a network 120. Embodiments of the computing environment 100 can have only one wearable sensor 140. Embodiments of the computing environment 100 can have multiple client devices 130, depth sensors 150, and external sources 160 connected to the network 120. Likewise, the functions performed by the various entities of FIG. 1 may differ in different embodiments.

A client device 130 is an electronic device used by a user to perform functions such as entering user data and events as input to the fall risk module 110 to train a model to quantify the user's fall risk. For example, the client device 110 may be a mobile device, a tablet, a notebook, a desktop computer, or a portable computer. The client device 110 includes interfaces with a display device on which the user may view webpages, videos and other content. In addition, the client device 110 provides a user interface (UI), such as physical and/or on-screen buttons with which the user may interact with the client device 110.

The wearable sensor 140 is an electronic device used to collect data from the user and wirelessly transmit the collected data over the network 120 to the fall risk module 110. Embodiments of the wearable sensor 140 are sensors including, but not limited to, inertial measurement units (IMU), accelerometers, gyroscopes, magnetometers, and photo diodes. Embodiments of the wearable sensor 140 may have form factors such as a wristband, wristwatch, pendant of a necklace, or belt clip, walking cane, and the like. The user can also have more than one sensor, such as one wristband and one walking cane sensor. Wearable sensors 140 can also track vital signs or biological or biometric data, including heart rate, breathing, temperature, blood pressure, etc.

The depth sensor 150 is an electronic device used to collect depth data from the user and wirelessly transmit the collected data over the network 120 to the fall risk module 110. Unlike the wearable sensor 140, the depth sensor 150 is located in a stationary position in the vicinity of or near the user. For example, the depth sensor 150 can be positioned near a television in the user's home. The depth sensor 150 (e.g., a camera) may record video, record audio, take photos, capture other media content about the user and the user's environment, and other forms of depth data. For example, this sensor 150 can be used to record the user's gait as the user walks, the user's standing posture, lighting conditions in the user's room, compliance by the user with doctor-prescribed walking assistance device (canes, walkers, etc.), daily activity types by the user, daily activity duration, among other information. Other types of sensors can also be included in the room, such as temperature sensors to determine temperature in the room, light sensors to detect room lighting conditions, etc. There can be a sensor 150 in multiple rooms of the user's home.

The network 120 enables communications among network entities such as the fall risk module 110, client device 130, wearable sensors 140, depth sensor 150, and external source 160. In one embodiment, the network 120 includes the Internet and uses standard communications technologies and/or protocols, e.g., BLUETOOTH®, WIFI®, ZIGBEE®, clouding computing, other air to air, wire to air networks, and mesh network protocols to client devices, gateways, and access points. In another embodiment, the network entities can use custom and/or dedicated data communications technologies.

The external source 160 provides information to the fall risk module 110 to train the model to quantify the user's fall risk. For example, the information can include data from a population of both healthy and unhealthy users, as well as medical practice standards (e.g., prescribing guidelines of consensus practice recommendations for reducing fall risk). In some embodiments, the information provided by the external source 160 is collected each time a fall risk score is determined by the fall risk module 110. In other embodiments, the fall risk module 110 builds up one or more of its own databases (e.g., see FIG. 2) of information about the population of users either in advance or as fall risk scores are determined such that the fall risk module 110 can utilize its own source of information about the user population. Such a fall risk module database can be updated regularly to ensure the most accurate and up-to-date information is kept on hand.

The external source 160 may also include historical health data of a user (e.g., a user's electronic medical records, or EMRs) from various health record sources (e.g., hospital records, records at the user's family doctors, or manually inputted data related to the user's health by the user's caretakers). The historical health data of a user describes a global view of the user's lifestyle and wellness. For example, the historical health data may include information about the user's vision, such as the user's eyeglass or contact prescription, whether the user has cataracts, glaucoma, or other eye-related conditions, results of annual vision examinations by a doctor, among other types of data. The historical health data could also include information about any conditions the user has that could affect the risk of falls for that individual, such as Parkinson's disease, factors in the user's medical history that might affect the user's balance (e.g., ear infections or other ear conditions, posture or back issues such as scoliosis, problems with legs, feet, or knees such as a prior knee injury, among other data).

The fall risk module 110 processes user inputs, data from the wearable sensor 140, data from the depth sensor 150, data from the external source 160, and/or data from a local database, and trains a machine learning model to determine a fall risk score for the user. The user inputs are provided by the user via the client device 130 (or in some cases via the wearable device holding the wearable sensor, such as a wristwatch) and include information such as their age, history of previous falls, vision, any use of assistive devices, lighting conditions, history of neurological disorders, and the like. In one embodiment, based on the determined fall risk score, the fall risk module 110 provides information to the user or a person associated with the user such as the user's caretaker, physician, family and friends, and the like. The information may include a prediction of the user's fall risk and/or a recommendation regarding how the user can reduce his or her risk of falling. The fall risk module 110 is further described below and with reference to FIGS. 2-6.

Fall Risk Module

Figure 2:
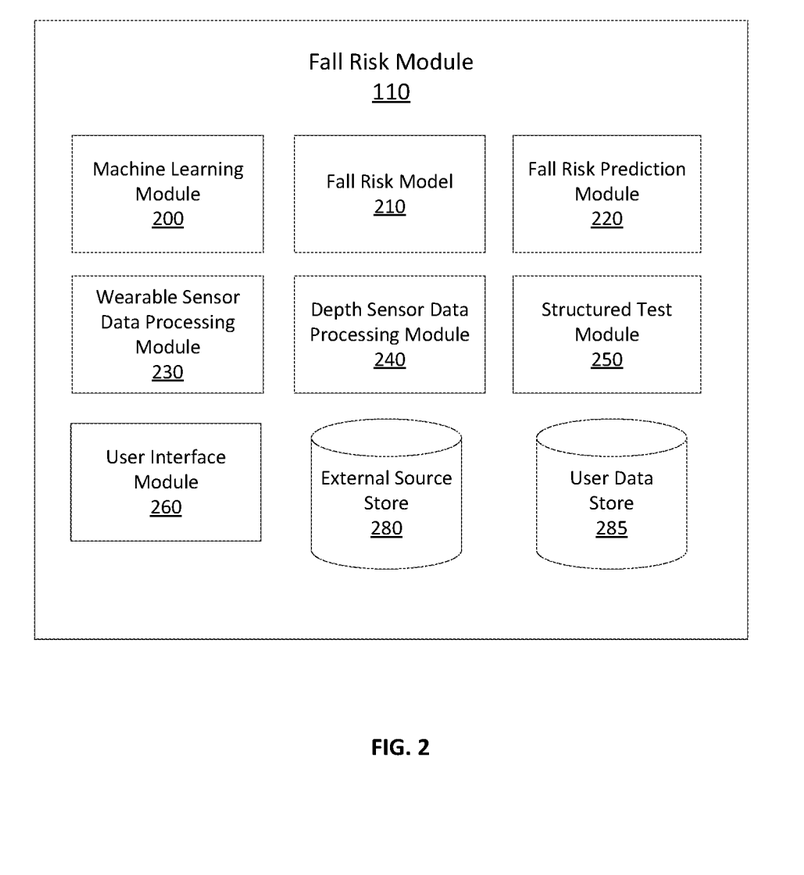
FIG. 2 is a block diagram of a fall risk module of an adaptive system to automatically quantify fall risk, according to one embodiment.

FIG. 2 is a block diagram of a fall risk module 110 of an adaptive system to automatically quantify fall risk, according to one embodiment. The fall risk module 110 assesses the fall risk of the user and generates recommendations regarding ways that the user can reduce his or her risk of falling. In the embodiment illustrated in FIG. 2, the fall risk module 110 has a machine learning module 200, fall risk model 210, fall risk prediction module 220, wearable sensor data processing module 230, depth sensor data processing module 240, structured test module 250, user interface module 260, external source store 280, and user data store 285. In alternative configurations, different, fewer, and/or additional components may be included in the fall risk module 110. For example, the fall risk module may integrate with various third party hardware or software to provide a comprehensive solution to users of the fall risk module 110. Functionality of one or more of the components may be distributed among the components in a different manner than is described herein.

The machine learning module 200 uses machine learning techniques to generate the fall risk model 210. In an embodiment, the machine learning module 200 may generate a model based on optimization of different types of fall risk scoring models, including but not limited to algorithms that analyze processed and/or raw data from each wearable sensor separately, or in any combination with processed data from the depth sensor, data from user inputs, or data from structured tests. For example, the machine learning module 200 may generate a classifier that takes as input a gait profile measured by motion sensors for a user and returns true if the determined fall risk based on the gait profile is greater than that of the average population and false otherwise. The fall risk prediction model 220 can use the output of the generated classifier to generate a fall risk score and/or predicted time period during which the user is more vulnerable to experience a fall. Other embodiments can use other machine learning techniques for determining fall risk, for example, tree-based models, kernel methods, convolutional neural networks, splines, or an ensemble of one or more of these techniques.

In some embodiments, the fall risk module 110 may use multiple fall risk models 210 for determining the fall risk for users. For example, the machine learning module 200 may divide the set of users of the fall risk module 100 into different subsets of users and generate one fall risk model 210 for each subset of user. The subsets of users may be determined based on demographic information describing the users, for example, age, gender, ethnic background, etc. Since different sets of users may have different characteristics determining their fall risk, a fall risk model 210 for each set of users is likely to provide more accurate score compared to a single fall risk model 210 for the entire set of users.

In an embodiment, the features used for a model for a set of users may depend on the value of the attribute that characterizes the set. For example, if the frequency of previous falls is used as an attribute that characterizes the set, different sets may be determined for users in a group that frequently experiences falls and users in a group that have never experienced a fall. The features used for the model for each set may depend on the frequency of falls for the set. For example, the model for a set of users who typically experience a fall once a month may use the times of day during which the users' previous falls occurred as a feature. In another different example, a model for a set of users who have never fallen may use the users' gait profiles as a feature.

The fall risk prediction model 220 generates and provides a prediction of a user's fall risk to the user interface manager 260 for presentation to the user via the client device 130. A person associated with the user (e.g., the user's caregivers and other health care providers, family and friends, and the like) may also view the fall risk on the client device. In addition to the fall risk, the fall risk prediction model 220 also generates feedback, using information from the external source store 280 and user data store 285, for presentation to the user, including recommendations regarding how the user can reduce their risk of falling, and how the user's fall risk compares with those of the population as a whole. For example, if the user has poor posture that is tied to a greater risk of falling, the fall risk prediction model 220 may notify the user and/or another clinician that the user's fall risk is greater than average and suggest that the user use a walking cane to reduce their fall risk. Other examples of recommendations include suggestions to change conditions in a user's environment, such as adjusting poor lighting conditions to provide more light to the user to avoid trips and falls, removal of items on the floor that present tripping hazards, adjustment of furniture in the room to avoid blocking common walkways and avoid bumping into furniture, providing better lighting at stairs or a step between two levels in a home, and so forth. Further examples including suggestions to a user to change posture or gait, such as focusing on standing up straighter, providing back strengthening exercises to improve posture, suggesting wearing of a back brace or knee brace to address the source of poor posture, recommending walking slower or taking smaller steps, recommending more swinging of your arms to improve balance, suggesting particular canes or walkers to address the person's particular issue with their gait, etc. A person associated with the user may also be notified of the user's fall risk and corresponding recommendations.

The wearable sensor data processing module 230 takes as input the data collected by the wearable sensor 140 and processes them to generate features used by the machine learning module 200. For example, 3-axis (e.g., x, y, and z) data from the inertial measurement unit (IMU) in the wearable sensor 140 can be processed to generate a gait profile of the user. Further, the IMU data can also be processed to identify when the user has experienced a fall. In another example, data from a photo diode in the wearable sensor 140 can be processed to generate the heart rate and pulse of the user. The gait profile, events such as a fall, heart rate, pulse, and other information associated with the user generated by the wearable sensor data processing module 230 is stored in the user data store 285.

The depth sensor data processing module 240 takes as input the data collected by the depth sensor 150 and processes them (e.g., using video processing techniques known to one skilled in the art) to generate features used by the machine learning module 200. For example, a recording of the user in a standing position can be processed (e.g., using skeletal tracking algorithms) to generate a model of the user's posture and determine the user's center of gravity. Further, the depth sensor data can also be processed to identify when the user changes from a sitting position to a standing position. The user's posture, center of gravity, transition from sitting to standing positions, and other information associated with the user generated by the depth sensor data processing module 240 is stored in the user data store 285.

The structured test module 250 prompts the user to complete a structured test, for example, to measure the trace of any swaying motions while the user is standing or to improve posture through regular strength training. The structured test module 250 provides instructions regarding the structured test to the user interface manager 260 for presentation to the user via the client device 130 or via a wearable device that holds the wearable sensor 140. The prompt occurs at a predetermined frequency (e.g., daily and weekly) and the user may be prompted to complete different structured tests at varying frequencies. The data recorded by the wearable sensor 140 and depth sensor 150 while the user is completing the structured test is processed by the wearable sensor data processing module 230 and depth sensor data processing module 240, and are used as features to train the fall risk model 210 and to update fall risk predictions. Data recorded during the structured test can be stored in the user data store 285. The structured tests may vary daily and may be presented to the user one at a time or in a set of one or more tests. Further, the structured tests selected for users, and the parameters of the selected tests, may be customized to each user based on information associated to each particular user. The structured test module 250 may provide live feedback to the user during and/or after completing the test. Information from feedback from the user during and/or after completing the test may be used to train the fall risk model 210.

In one embodiment of the structured test, the structured test module 250 sends a text message notification via a smart phone client device 130 each morning to a user, who is wearing a wristwatch with a wearable sensor 140, requesting that the user complete a mean radius of trace test. The user opens a software application on the smart phone to begin the test. The user also has the option to postpone the test via the software application. The software application receives audible instructions and visual instructions from the structured test module 250 and provides audible instructions via the speakers of the smart phone and visual instructions via the user interface of the smart phone to the user, guiding the user through the steps of the test. For the first step of the test, the structured test module 250 instructs the user to stand up, and the wearable sensor 140 collects data indicating the user's starting position. For the second step, the structured test module 250 instructs the user to remain standing for a continuous ten second period. A count down timer is displayed on the smart phone indicating the remaining duration of the ten second period. Once the ten second period has elapsed, the smart phone provides a visual message and audio message indicating that the test is complete. Data collected from the wearable sensor 140 during the test is used to calculate a mean radius of trace, which indicates how much the user swayed while standing. If data processed from previous tests completed by the user indicate that the user has a low mean radius of trace, which suggests that the user has strong postural stability, the user may be prompted less frequently to complete this test in the future. On the other hand, if data processed from previous tests completed by the user indicate that the user has a large mean radius of trace, which suggests that the user has weak postural stability, the ten second period may be adjusted to a shorter or longer time period of time in future tests.

In another embodiment of the structured test, the structured test module 250 measures the heart rate and/or pulse of the user while the user is sitting down or in a recumbent position and again immediately after the user has stood up. Heart rate and pulse data may be collected by an infrared-light based sensor included in the wearable sensor 140. The fall risk module 110 calculates the difference between the heart rate and/or pulse measurements before and after the user has stood up. A large calculated difference can suggest that the user may have postural hypotension, which is associated with a low blood pressure drop that occurs when an individual stands up from a sitting or recumbent position. After the user stands up during this test, the structured test module 250 may immediately prompt the user via the client device 130 to indicate whether the user feels lightheaded, which is a common symptom of individuals with postural hypotension when they stand up.

The external source store 280 stores information from the external source 160 including, but not limited to, data from a population of both healthy and unhealthy users, as well as medical practice standards. Data from a population of both healthy and unhealthy users may include statistics regarding the mean and standard deviation of the number of falls per week for both groups of users categorized as healthy and unhealthy, among other data. The medical practice standards may include recommending an increase in fluid and dietary salt intake to users who have postural hypotension as an identified risk factor. Other examples of medical practice standards stored in the source 160 include recommending physical balance therapy for users who suffer from postural instability, and advising to avoid interactions between different sedative medications for users who demonstrate chronic use of sedatives from their medical history, among other data.

Mean Radius of Trace Detection

Figure 3A:
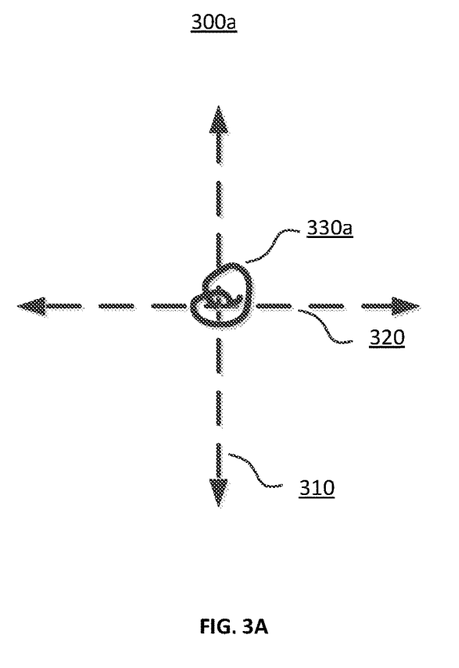
FIG. 3A is a chart illustrating the trace of a healthy user with a fall risk near average as measured by the adaptive system to automatically quantify fall risk, according to one embodiment.

FIG. 3A is a chart 300a illustrating the trace of a healthy user with a fall risk near average as measured by the adaptive system to automatically quantify fall risk, according to one embodiment. The trace 330a represents any swaying motions of the healthy user while in a standing position and is mapped on a 2D plane parallel to the ground with an x-axis 320 and y-axis 310. In alternate embodiments, the trace 330a can be mapped to combinations of different axis in a 2D plane, mapped in 3D, or mapped in a 1D line. The trace 330a can be generated using data processed by the wearable sensor data processing module 230 and/or depth sensor data processing module 240 collected by the wearable sensor 140 and/or the depth sensor 150. This information may be collected for the user during a structured test where the user is asked to stand in one position and the sway of the user is measured for a period of time, or this information may be collected throughout the day as the user stands or moves. The mean radius of trace from the origin of 2D plane can be calculated by the fall risk module 110 based on the trace 330a and averaging the distance that the user deviated from a starting position, in the case of a structured test, or from a determined average or reference position, in cases outside of a structured test, over a period of time. The mean radius of trace is compared against the mean radius of trace for a larger population of users and/or that of an unhealthy user. For a healthy user, the trace 330a is expected to show only small motions in the 2D plane.

Figure 3B:
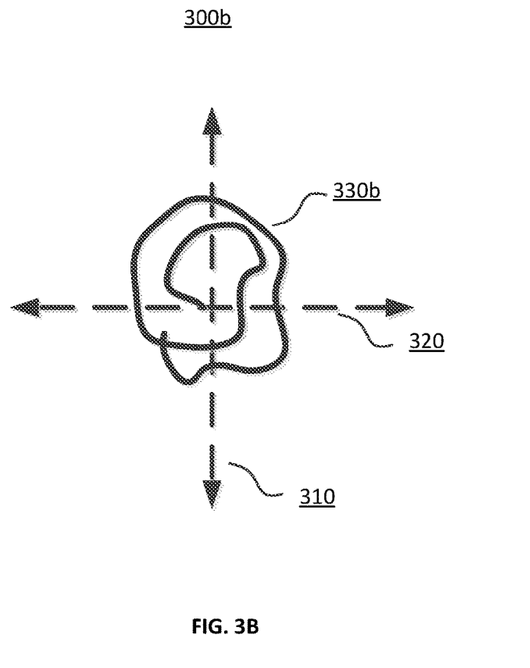
FIG. 3B is a chart illustrating the trace of an unhealthy user with a fall risk greater than average as measured by the adaptive system to automatically quantify fall risk, according to one embodiment.

FIG. 3B is a chart illustrating the trace of an unhealthy user with a fall risk greater than average as measured by the adaptive system to automatically quantify fall risk, according to one embodiment. The trace 330b represents any swaying motions of the unhealthy user while in a standing position and is mapped on a 2D plane parallel to the ground with an x-axis 320 and y-axis 310. In alternate embodiments, the trace 330b can be mapped to combinations of different axis in a 2D plane, mapped in 3D, or mapped in a 1D line. The trace 330a can be generated using data processed by the wearable sensor data processing module 230 and/or depth sensor data processing module 240 collected by the wearable sensor 140 and/or the depth sensor 150. The mean radius of the trace from the origin of 2D plane can be calculated by the fall risk module 110 based on the trace 330a and averaging the distance that the user deviated from a starting position, in the case of a structured test, or from a determined average or reference position, in cases outside of a structured test, over a period of time. The mean radius of trace is compared against the mean radius of the trace for a larger population of users and/or that of a healthy user. For an unhealthy user, the trace 330a is expected to show larger motions, relative to those of a healthy user, in the 2D plane. For example, unhealthy users with multiple sclerosis typically have symptoms of poor balance, which would result in larger swaying motions while standing and thus, a greater mean radius of the trace. The machine learning module 200 can use data from the traces of the unhealthy and the healthy user to train the fall risk model 210, which may influence the generated fall risk scores.

In other embodiments, the trace 330a and the trace 330b can represent the anterior, posterior, medial, and lateral coordinates of the user's body while attempting to stand still. The 2D plane may correspond to the sagittal plane (i.e., the plane parallel to the sagittal suture of the human body), the frontal/coronal plane (i.e., the plane that divides the human body into the back and front, or posterior and anterior, sections), and the transverse plane (i.e., the plane that divides the human body into the cranial and caudal, or head and tail, sections). The trace 330a and the trace 330b may be mapped in 3D onto any combination of two or more of these three 2D planes. The mean radius of trace can be calculated in any combination of one, two, or three dimensions. The chart 300a and the chart 300b may also show the pitch, roll, and yaw angles exhibited as the user is swaying, which can be demonstrative of balance difficulties or disorders. The machine learning module 200 can use these three angles from the user to train the fall risk model 210, which may influence the generated fall risk scores.

Center of Gravity Detection

Figure 4A:
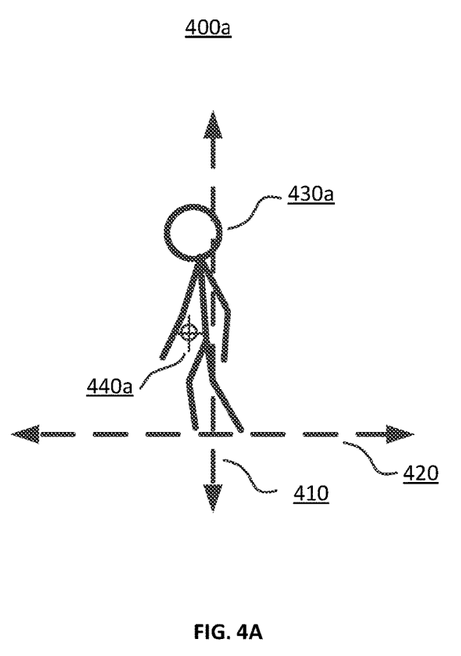
FIG. 4A is a diagram illustrating the posture and center of gravity of a healthy user with a fall risk near average as measured by the adaptive system to automatically quantify fall, risk, according to one embodiment.

FIG. 4A is a diagram illustrating the posture and center of gravity of a healthy user with a fall risk near average as measured by the adaptive system to automatically quantify fall, risk according to one embodiment. The healthy user's standing posture 430a is mapped on a 2D plane orthogonal to the ground with an x-axis 420 and z-axis 410. In alternate embodiments, the posture 430a can be mapped to combinations of different axis in a 2D plane, mapped in 3D, or mapped in a 1D line. The posture 430a can be generated using data processed by the wearable sensor data processing module 230 and/or depth sensor data processing module 240 collected by the wearable sensor 140 and/or the depth sensor 150. The healthy user's center of gravity 440a can be calculated by the fall risk module 110 based on the posture 430a and compared against the center of gravity of a standing posture for a larger population of users and/or that of an unhealthy user. For a healthy user, the center of gravity 440a is expected to be close to the z-axis 410 because the user will be standing upright. The center of gravity information may be collected during a structured test performed by a user or may be collected throughout the day.

Figure 4B:
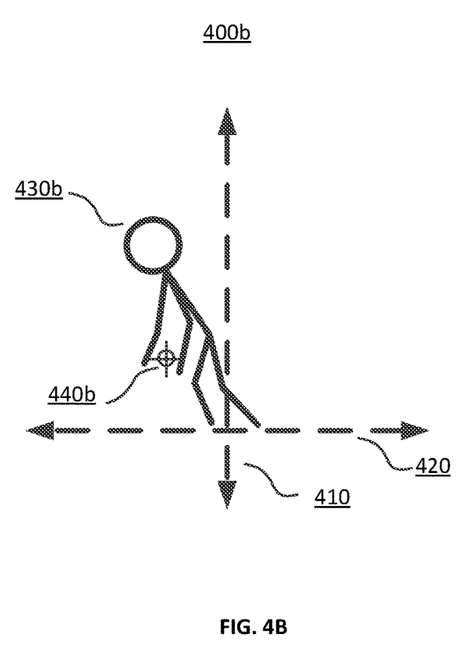
FIG. 4B is a diagram illustrating the posture and center of gravity of an unhealthy user with a fall risk greater than average as measured by the adaptive system to automatically quantify fall risk, according to one embodiment.

FIG. 4B is a diagram illustrating the posture and center of gravity of an unhealthy user with a fall risk greater than average as measured by the adaptive system to automatically quantify fall risk, according to one embodiment. The unhealthy user's standing posture 430b is mapped on a 2D plane orthogonal to the ground with an x-axis 420 and z-axis 410. In alternate embodiments, the posture 430b can be mapped to combinations of different axis in a 2D plane, mapped in 3D, or mapped in a 1D line. The posture 430b can be generated using data processed by the wearable sensor data processing module 230 and/or depth sensor data processing module 240 collected by the wearable sensor 140 and/or the depth sensor 150. The unhealthy user's center of gravity 440b can be calculated by the fall risk module 110 based on the posture 430b and compared against the center of gravity of a standing posture for a larger population of users and/or that of a healthy user. For an unhealthy user, the center of gravity 440b is expected to be further from the z-axis 410 because the user may not be standing upright. For example, unhealthy users with Parkinson's have symptoms of postural instability, which typically results in a forward or backward lean with the drooped shoulders and a bowed head. Since the postural instability can cause the unhealthy user to experience more falls, the determined center of gravity 440b can be used by the fall risk module 110 to generate a greater fall risk score for the unhealthy user.

Machine Learning Module

Figure 5A:
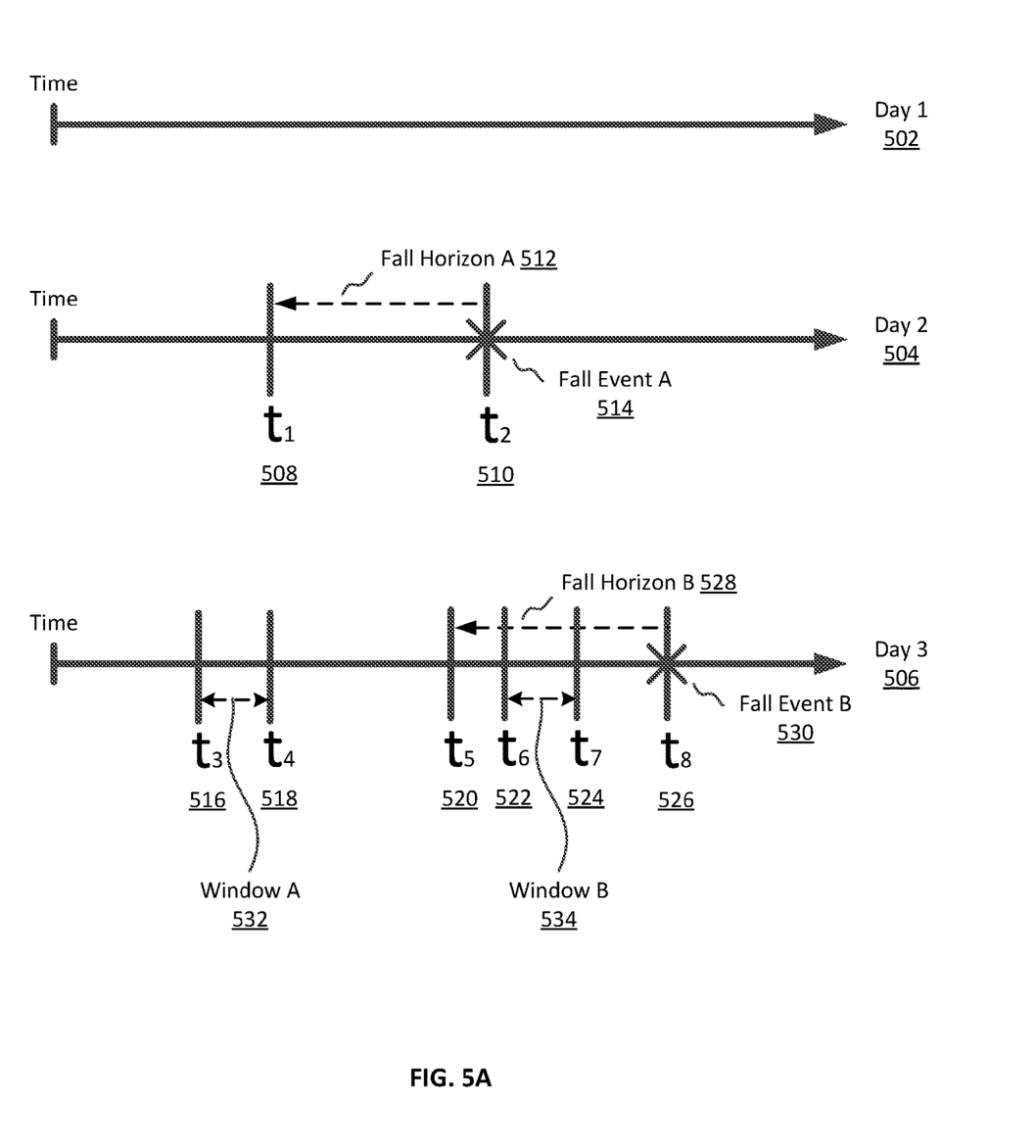
FIG. 5A shows a diagram illustrating timelines with fall events of a user, according to one embodiment.

FIG. 5A shows a diagram illustrating timelines with fall events of a user, according to one embodiment. In the embodiment illustrated in FIG. 5A, there are three timelines each representing a different day during which the fall risk module 110 receives data from a user. The days may be subsequent days or days separated by more than one day. In day 1 502, the fall risk module 110 does not receive data indicating that the user has experienced a fall event. In day 2 504, the fall risk module 110 receives data indicating that the user has experienced a fall event A 514, represented by the cross mark on the timeline at time $t_2$ 510. The fall horizon A 512 represents the period of time immediately preceding the fall event A 514. The fall horizon A 512 is a predetermined duration of time from time $t_1$ 508 to time $t_2$ 510. In day 3 506, the fall risk module 110 receives data indicating that the user has experienced a fall event B 530, represented by the cross mark on the timeline at time $t_8$ 526. Fall event B 530 corresponds with fall horizon B 528, which starts at time $t_5$ 520. In day 3 506, window A 532 is the period of time starting from time $t_3$ 516 and ending at time $t_4$ 518, and window B 534 is the period of time starting from time $t_6$ 522 and ending at time $t_7$ 524. Window A 532 and window B 534 may be the same or different duration of time (e.g., both windows can be 30 seconds in duration), and in other embodiments, different windows may overlap in a timeline. In the embodiment illustrated in FIG. 5A, Window A 532 does not fall within fall horizon B 528, while window B 534 does fall within fall horizon B 528. Data collected from sources such as the client device 130, wearable sensors 140, depth sensors 150, and/or external sources 160 during window A 532, window B 534, and additional windows representing periods of time in the timeline of a day may be used by the fall risk module 110 to generate a tensor, which is further described in FIG. 5B, to train the fall risk model 210, which may influence the generated fall risk scores.

Figure 5B:
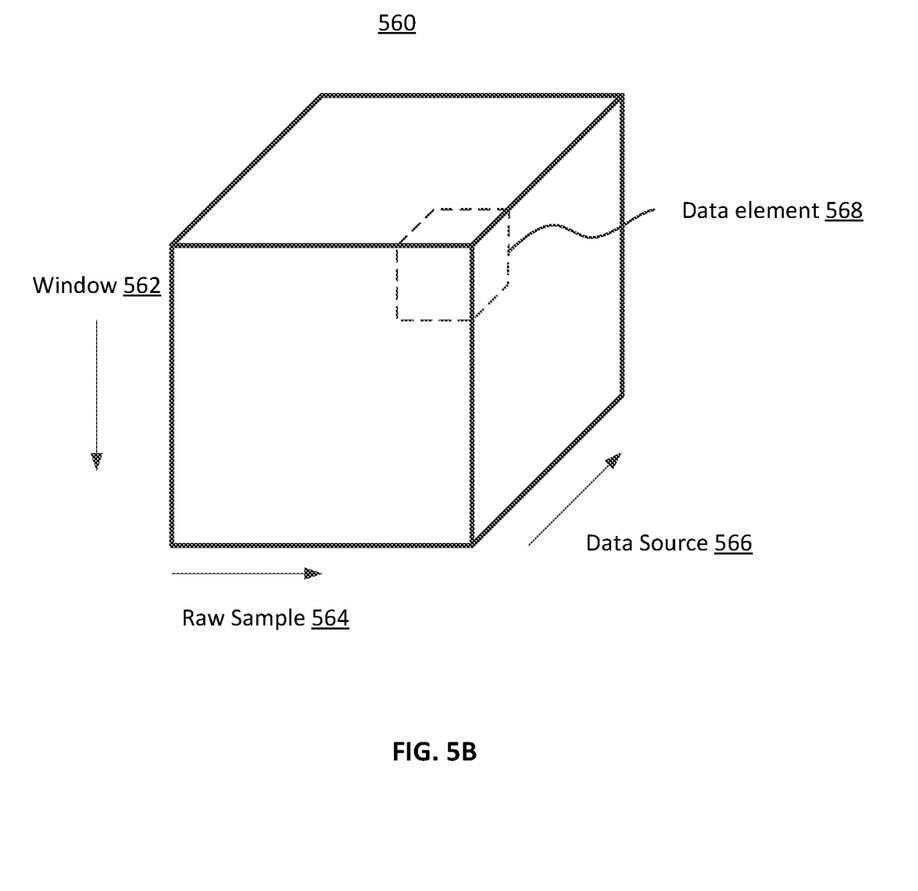
FIG. 5B shows a diagram illustrating a tensor of data used by a fall risk module, according to one embodiment.

FIG. 5B shows a diagram illustrating a tensor 560 of data used by a fall risk module 110, according to one embodiment. In the embodiment illustrated in FIG. 5B, the tensor 560 is represented by a matrix with three dimensions. The first dimension, window 562, represents one or more windows (i.e., periods of time) during which the fall risk model 210 received data corresponding to a user. The second dimension, raw sample 564, represents one or more raw data samples during which the fall risk model 210 received data corresponding to a user. The third dimension, data source 566, represents one or more sources of data from which the fall risk model 210 received data corresponding to a user. The sources of data may include devices such as the client device 130, wearable sensors 140, and depth sensor 150, as well as other sources such as external sources 160. Further, the source of data may be a specific channel of data from a device, for instance, the x-axis channel of a 3-axis accelerometer and/or gyroscope, or any combination of channels of data from a device, for instance, the roll, pitch, and yaw angles from an inertial measurement unit. The data element 568 represents one data element in the tensor 560. In one example, the data element 568 may be collected from the first window of data in the window 562 dimension, the last raw sample in the raw sample 564 dimension, and the data source that corresponds to the x-axis channel of an accelerometer in the data source 566 dimension. The value of the data element may be a numerical value, clear text, Boolean, or other representations of data. Following in the same example above, the data element from an x-axis channel of an accelerometer may be a numerical value from 0 to 255. One or more tensors 560 may be used to determine features, further described in FIG. 5C, to train the fall risk model 210.

In other embodiments, the tensor 560 may have fewer, more, and/or different dimensions. For example, instead of the raw sample 564 dimension, the tensor 560 may have a dimension representing one or more processed data samples during which the fall risk model 210 received data corresponding to the user. In another example, instead of the window 562 dimension, the tensor 560 may have a dimension representing one or more structured tests completed by the user during which data from the user was received by the fall risk model 210.

Figure 5C:
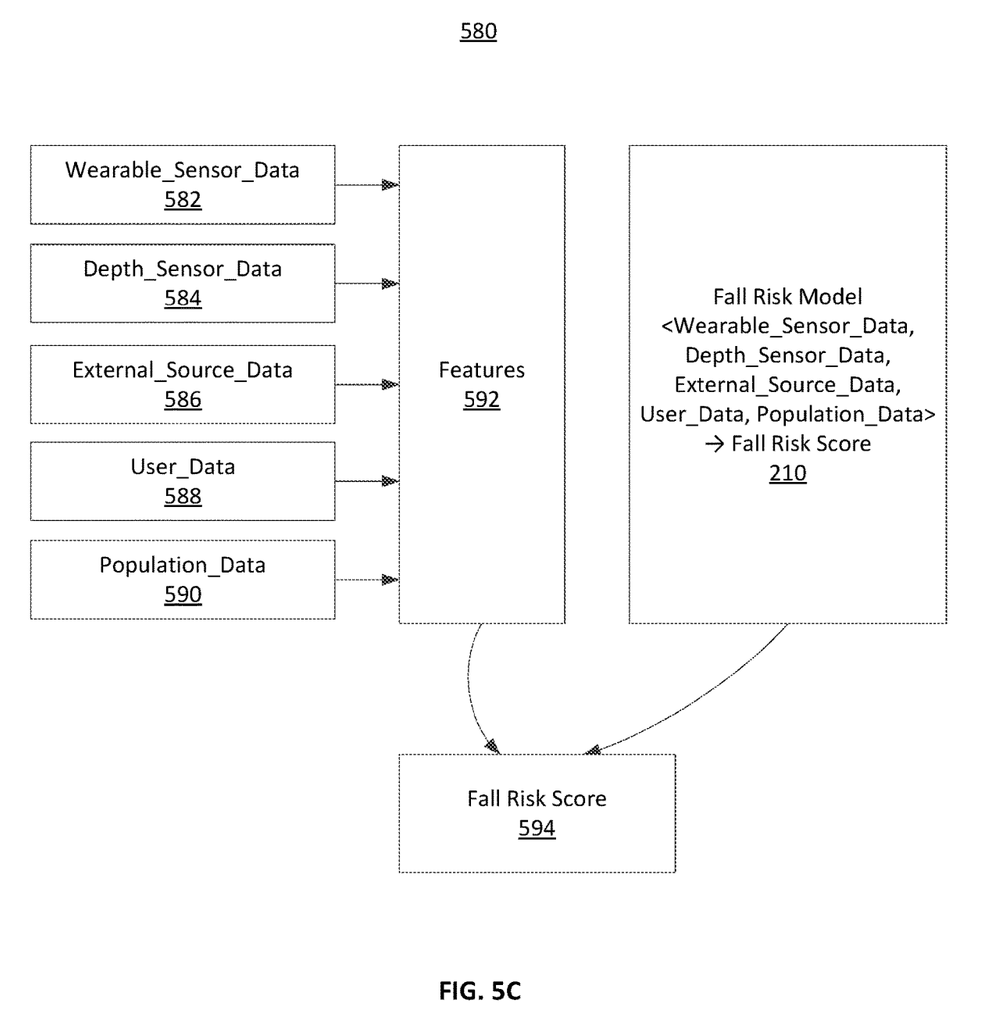
FIG. 5C shows a data flow diagram illustrating the interactions between various types of data used to determine a fall risk score, according to one embodiment.

FIG. 5C shows a data flow diagram 580 illustrating the interactions between various types of data used to determine a fall risk score, according to one embodiment. As shown in FIG. 5, the fall risk model 210 trained by the machine learning module 200 is used to determine a fall risk score 594 for the user. The machine learning module 200 may extract features 592 from data including wearable_sensor_data 510 from the wearable sensors 140, depth_sensor_data 520 from the depth sensor 150, external_source_data 530 from the external source 160 and/or external source store 280, user_data 540 from the client device 130 and/or user data store 285, and population_data 550 from the external source 160 to use as training data sets to train the fall risk model 210. The machine learning module 200 may also extract features 592 from the tensor 560. Further, an expert may manually provide features and training data sets to the fall risk model 210 (e.g., through the client device 130). For example, a data scientist may discover features or motifs that are associated with fall events.

In one instance, referring back to day 3 506 illustrated in FIG. 5A, the data scientist discovers from the data of a user collected by wearable sensors 140 that the user was eating a meal during window B 534, but the user did not take prescribed medication recommended to be taken with the meal. Since the user experienced fall event B 530 shortly following the meal during window B 534, the data scientist may determine that eating a meal without taking prescribed medication may be a feature that predicts a higher risk of a fall event occurring. After this feature is provided to the fall risk module 110, the machine learning module 200 may perform a retrospective identification of fall events by searching for occurrences of this feature in previously collected data (e.g., data from day 2 504 and day 1 502). Results of the retrospective identification may either reinforce or weaken the feature for training the fall risk model 210 depending on how strongly the feature is correlated with occurrences of fall events.

In another instance, once the fall risk model 210 has been trained with an initial training data set, the machine learning module 200 uses machine learning techniques known to one skilled in the art such as deep learning convolutional neural networks to identify additional features and motifs used to train the fall risk model 210 and predict fall risk. For example, using a neural network, the machine learning module 200 may identify a particular pattern from data in the tensor 560 involving a combination of data from multiple accelerometer and gyroscope axis channels that often precedes a fall event. The features and motifs identified by the machine learning module 200 or an expert (e.g., a data scientist) may be used by the fall risk module 110 to generate a machine learning classifier to predict a user's fall risk.

In one embodiment, a classifier generated by the fall risk module 110 predicts whether each window of collected data in the tensor 560 falls within a fall horizon or does not fall within a fall horizon. For example, referring back to day 3 506 illustrated in FIG. 5A, predicting that window B 534 falls within a fall horizon would be a correct prediction because window B 534 falls within fall horizon B 528. The classifier, which may be used by the fall risk model 210 and/or fall risk prediction module 220, determines a score based on an input window of a tensor 560 and compares the score against a threshold value. If the score is above the threshold, the classifier predicts that the window falls within a fall horizon; otherwise, the classifier predicts that the window does not fall within a fall horizon. The threshold may be adjusted over time based on the accuracy of the classifier as determined using retrospective analysis or manual input from an expert. For example, if the classifier is causing too many false positives (e.g., incorrect predictions of windows falling within a fall horizon), the fall risk module 110 may increase the threshold value. On the other hand, if the classifier is causing too many false negatives (e.g., incorrect predictions of windows not falling within a fall horizon), the fall risk module 110 may decrease the threshold value.

Figure 6:
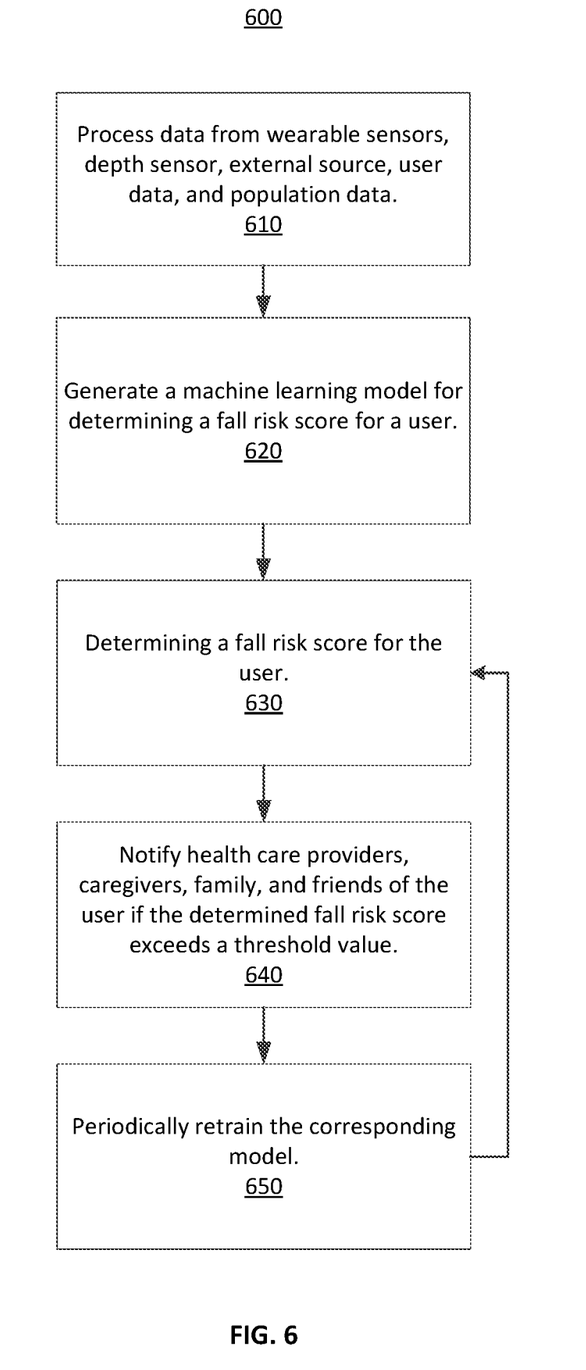
FIG. 6 is a flowchart of the process of periodically retraining a model for determining a fall risk score for a user, according to one embodiment.

FIG. 6 is a flowchart of the process 600 of periodically retraining a model for determining a fall risk score for a user, according to one embodiment. The fall risk module 110 receives/collects and processes 610 data from the wearable sensors 140, depth sensor 150, external source 160, user data, and population data. The machine learning module 200 generates 620 a machine learning model (e.g., the fall risk model 210) for determining fall risk scores corresponding to each subset of users. The generation 620 of the fall risk model 210 may comprise training the fall risk model 210 based on a training data set and/or a tensor 560. An expert may analyze various the features 592 and determine which particular features correlate to a greater or lower fall risk. For example, a high mean radius of trace that indicates a user demonstrates large swaying motions while standing may be correlated to a greater fall risk. In another example, a center of gravity in standing posture that indicates a user leaning forward may also be correlated to a greater fall risk. On the other hand, a lower fall risk may be correlated to a user who has a gait profile similar to the average gait profile of a healthy user in the general population. Based on the trained fall risk model 210 and data from one or more tensors 560, the fall risk module 110 determines 630 a fall risk score (e.g., fall risk score 594) for the user.

If the determined fall risk score exceeds a threshold value, then the fall risk module 110 notifies 640 a combination of the health care providers, caregivers, family, and friends of the user, as well as any other person associated with the user regarding the score. The notification may be in the form of an automatically generated electronic message (e.g., text message and email) sent to the client device 130. The threshold value may be set by the expert, based on the external source 160, based on the tensor 560 processed by the machine learning module 200, or based on another person or source of information.

The machine learning module 200 periodically retrains 650 the model corresponding to each subset of users. The machine learning module 200 may retrain each model at a fixed frequency. The model corresponding to each subset may be retrained 650 at a different frequency compared to other models. The machine learning module 200 may use information describing how users of each subset interact with the fall risk module 110 via the client device 130, or data from the tensor 560, to determine a rate at which the corresponding model is retrained 650. After the model is retrained 650, the fall risk module 110 again determines 630 a fall risk score (e.g., fall risk score 594) for the user, which may be different than the previously determined score because the model has been updated.

Alternative Applications

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method comprising:
    conducting a structured test with a user, the structured test including presenting an instruction to the user to perform at least one action to test a current state of the user;
    retraining a classifier based at least in part on data collected during the structured test, wherein the classifier is trained based on data about a plurality of users;
    receiving, from one or more sensors worn by the user or placed near the user, sensor data that indicates at least one environmental condition near the user;
    receiving, from the user or from records associated with the user, data about factors for the user;
    providing features based on the sensor data that indicates at least one environmental condition near the user, features based on sensor data received during the structured test, and features based on the factors for the user to the classifier to generate a score indicating a likelihood of whether an input window is within a fall horizon, wherein the fall horizon is a predetermined period of time that immediately precedes a fall event;
    determining that the score is greater than a predetermined threshold; and
    in response to the score being greater than the predetermined threshold, notifying a client device with information about a prediction of a fall risk of the user;
    wherein the structured test comprises a test for measuring a mean radius of trace of the user while standing, wherein presenting the instruction to the user to perform the at least one action to test the current state of the user includes providing an instruction to the user to stand up, and wherein the test comprises:
        measuring, with sensor data collected from the one or more sensors, a starting position of the user and the mean radius of trace of the user while the user is standing during a test duration, the mean radius of trace representing an average distance that the user deviated from the starting position over the test duration;
        adjusting a timing of providing a subsequent instruction to the user to stand up for a subsequent structured test based on the mean radius of trace; and
        adjusting the test duration to be shorter or longer for the subsequent structured test based on the mean radius of trace; and
    wherein providing features based on sensor data received during the structured test to the classifier includes providing the measured mean radius of trace to the classifier.

2. The method of claim 1, further comprising:
    generating a recommendation describing how the fall risk of the user can be reduced, wherein the recommendation is based at least in part on the received sensor data; and
    providing the recommendation to the user or a person associated with the user.

3. The method of claim 2, wherein the recommendation comprises a recommendation to change the at least one environmental condition near the user to reduce the fall risk of the user.

4. The method of claim 1, further comprising performing an activity classification based at least in part on the received sensor data, the activity classification used to determine an activity, a corresponding duration of the activity, and whether the user uses an assistive device based on a body position of the user.

5. The method of claim 1, wherein the one or more sensors comprise at least one depth sensor placed in a room in which the user is present, the at least one depth sensor taking measurements of a posture of the user while standing, the posture mapped to one or more axes to determine a center of gravity of the user, the center of gravity provided as a feature to the classifier.

6. The method of claim 1, wherein the data about factors for the user comprise information associated with a vision level of the user.

7. The method of claim 1, wherein the predetermined threshold is based at least in part on a mean and a standard deviation of a number of falls experienced by the plurality of users per a predetermined period of time.

8. The method of claim 1, wherein providing features based on the sensor data and the factors for the user to the classifier trained based on data about a plurality of users includes:
    generating a multi-dimensional matrix including at least one of the sensor data and the data about factors for the user, organized by dimension; and providing a feature identified using the multi-dimensional matrix to the classifier.

9. A computer program product stored on a non-transitory computer-readable medium that includes instructions that, in response to execution by a processor of a system, cause the system to perform actions comprising:
conducting a structured test with a user, the structured test including presenting an instruction to the user to perform at least one action to test a current state of the user;
retraining a classifier based at least in part on data collected during the structured test, wherein the classifier is trained based on data about a plurality of users;
receiving, from one or more sensors worn by a user or placed near the user, sensor data that indicates a movement of the user and at least one of a heart rate of the user and a pulse of the user;
providing features based on sensor data received during the structured test and features based on the sensor data that indicates the movement of the user and at least one of the heart rate of the user and the pulse of the user to the classifier to generate a score indicating a likelihood of whether an input window is within a fall horizon, wherein the fall horizon is a predetermined period of time that immediately precedes a fall event;
determining that the score is greater than a predetermined threshold; and
in response to the score being greater than the predetermined threshold, notifying a client device with information about a prediction of a fall risk of the user;
wherein the structured test comprises a test for measuring a mean radius of trace of the user while standing, wherein presenting the instruction to the user to perform the at least one action to test the current state of the user includes providing an instruction to the user to stand up, and wherein the test comprises:
measuring, with sensor data collected from the one or more sensors, a starting position of the user and the mean radius of trace of the user while the user is standing during a test duration, the mean radius of trace representing an average distance that the user deviated from the starting position over the test duration;
adjusting a timing of providing a subsequent instruction to the user to stand up for a subsequent structured test based on the mean radius of trace; and
adjusting the test duration to be shorter or longer for the subsequent structured test based on the mean radius of trace; and
wherein providing features based on sensor data received during the structured test to the classifier includes providing the measured mean radius of trace to the classifier.

10. The computer program product of claim 9, wherein the actions further comprise:
generating a recommendation describing how the fall risk of the user can be reduced, wherein the recommendation is based at least in part on the received sensor data; and
providing the recommendation to the user or a person associated with the user.

11. The computer program product of claim 9, wherein the actions further comprise performing an activity classification based at least in part on the received sensor data, the activity classification used to determine an activity, a corresponding duration of the daily activity, and whether the user uses an assistive device based on a body position of the user.

12. The computer program product of claim 9, wherein providing features based on the sensor data to the classifier trained based on data about a plurality of users includes:
generating a multi-dimensional matrix including at least one of the sensor data that indicates a movement of the user, the sensor data that indicates the heart rate of the user, and the sensor data that indicates the pulse of the user, organized by dimension; and
providing a feature identified using the multi-dimensional matrix to the classifier.

13. A system comprising:
a processor configured to execute instructions; and
a non-transitory computer-readable memory storing instructions executable by the processor and causing the system to carry out the steps of:
conducting a structured test with a user, the structured test including presenting an instruction to the user to perform at least one action to test a current state of the user;
retraining a classifier based at least in part on data collected during the structured test, wherein the classifier is trained based on data about a plurality of users;
receiving, from one or more sensors worn by the user or placed near the user, sensor data that indicates at least one environmental condition near the user;
receiving, from the user or from records associated with the user, data about factors for the user;
providing features based on the sensor data that indicates at least one environmental condition near the user, features based on sensor data received during the structured test, and features based on the factors for the user to the classifier to generate a score indicating a likelihood of whether an input window is within a fall horizon, wherein the fall horizon is a predetermined period of time that immediately precedes a fall event;
determining that the score is greater than a predetermined threshold; and
in response to the score being greater than the predetermined threshold, notifying a client device with information about a prediction of a fall risk of the user
wherein the structured test comprises a test for measuring a mean radius of trace of the user while standing, wherein presenting the instruction to the user to perform the at least one action to test the current state of the user includes providing an instruction to the user to stand up, and wherein the test comprises:
measuring, with sensor data collected from the one or more sensors, a starting position of the user and the mean radius of trace of the user while the user is standing during a test duration, the mean radius of trace representing an average distance that the user deviated from the starting position over the test duration;
adjusting a timing of providing a subsequent instruction to the user to stand up for a subsequent structured test based on the mean radius of trace; and
adjusting the test duration to be shorter or longer for the subsequent structured test based on the mean radius of trace; and wherein providing features based on sensor data received during the structured test to the classifier includes providing the measured mean radius of trace to the classifier.

14. The system of claim 13, further comprising:
generating a recommendation describing how the fall risk of the user can be reduced, wherein the recommendation is based at least in part on the received sensor data; and
providing the recommendation to the user or a person associated with the user.

15. The system of claim 13, further comprising performing an activity classification on the user based at least in part on the received sensor data, the activity classification used to determine an activity, a corresponding duration of the activity, and whether the user uses an assistive device based on a body position of the user.

16. The system of claim 13, wherein providing features based on the sensor data and the factors for the user to the classifier trained based on data about a plurality of users includes:
generating a multi-dimensional matrix including at least one of the sensor data and the data about factors for the user, organized by dimension; and
providing a feature identified using the multi-dimensional matrix to the classifier.

17. The method of claim 1, wherein at least one sensor is selected from the group consisting of: an inertial measurement unit, an accelerometer, a gyroscope, a magnetometer, and a photo diode.

18. The method of claim 2, wherein the recommendation includes at least one recommendation selected from the group consisting of: using an assistive walking device, changing standing posture or gait, changing an environmental condition, moving a tripping hazard, and exercising.

19. A computer-implemented method comprising:
conducting a structured test with a user, the structured test including presenting an instruction to the user to perform at least one action to test a current state of the user;
receiving, from one or more sensors worn by the user or placed near the user, sensor data that indicates at least one environmental condition near the user;
receiving, from the user or from records associated with the user, data about factors for the user;
collecting, from one or more external sources, data about a population fall risk of a population of users;
extracting features from at least the received sensor data, the data about factors for the user, and the data about the population fall risk of the population of users;
detecting, based on at least the received sensor data, a fall event;
training a machine learning model based at least in part on the extracted features based on sensor data received within a fall horizon and features based on sensor data received during the structured test, wherein the fall horizon is a predetermined period of time immediately preceding the detected fall event; and
providing the machine learning model for generating a score indicating a likelihood of whether features extracted during an input window indicate that the input window is within a future fall horizon, wherein the future fall horizon is a predetermined period of time immediately preceding a predicted future fall event;
wherein the structured test comprises a test for measuring a mean radius of trace of the user while standing, wherein presenting the instruction to the user to perform the at least one action to test the current state of the user includes providing an instruction to the user to stand up, and wherein the test comprises:
measuring, with sensor data collected from the one or more sensors, a starting position of the user and the mean radius of trace of the user while the user is standing during a test duration, the mean radius of trace representing an average distance that the user deviated from the starting position over the test duration;
adjusting a timing of providing a subsequent instruction to the user to stand up for a subsequent structured test based on the mean radius of trace; and
adjusting the test duration to be shorter or longer for the subsequent structured test based on the mean radius of trace; and
wherein training the machine learning model based at least in part on features based on sensor data received during the structured test includes training the machine learning model based at least in part on the measured mean radius of trace.

20. The method of claim 6, wherein the sensor data that indicates at least one environmental condition near the user includes sensor data that indicates a lighting condition near the user.

* * * * *